United States Patent
Sumi et al.

(10) Patent No.: US 11,766,209 B2
(45) Date of Patent: Sep. 26, 2023

(54) COGNITIVE FUNCTION EVALUATION DEVICE, COGNITIVE FUNCTION EVALUATION SYSTEM, AND COGNITIVE FUNCTION EVALUATION METHOD

(71) Applicant: Panasonic Intellectual Property Management Co., Ltd., Osaka (JP)

(72) Inventors: Sadayuki Sumi, Hyogo (JP); Kengo Abe, Nara (JP); Ryosuke Nagumo, Osaka (JP); Takashi Nishiyama, Hyogo (JP); Yoshihiro Matsumura, Osaka (JP); Takaaki Ukeda, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 569 days.

(21) Appl. No.: 16/634,863

(22) PCT Filed: Jul. 20, 2018

(86) PCT No.: PCT/JP2018/027230
§ 371 (c)(1),
(2) Date: Jan. 28, 2020

(87) PCT Pub. No.: WO2019/044255
PCT Pub. Date: Mar. 7, 2019

(65) Prior Publication Data
US 2020/0229752 A1 Jul. 23, 2020

(30) Foreign Application Priority Data

Aug. 28, 2017 (JP) .................. 2017-163795

(51) Int. Cl.
*A61B 5/00* (2006.01)
*G10L 25/66* (2013.01)

(52) U.S. Cl.
CPC .......... *A61B 5/4088* (2013.01); *A61B 5/4803* (2013.01); *A61B 5/7278* (2013.01); *A61B 5/742* (2013.01); *G10L 25/66* (2013.01)

(58) Field of Classification Search
None
See application file for complete search history.

(56) References Cited

U.S. PATENT DOCUMENTS 7,756,703 B2 * 7/2010 Lee .................. G10L 25/48
704/219
2006/0282004 A1 * 12/2006 Kraus .................. A61B 5/38
600/544

(Continued)

FOREIGN PATENT DOCUMENTS

CN 102498485 A 6/2012
JP 2004-240394 A 8/2004

(Continued)

OTHER PUBLICATIONS

Skodda, Sabine, Wenke Grönheit, and Uwe Schlegel. "Impairment of vowel articulation as a possible marker of disease progression in Parkinson's disease." PloS one 7.2 (2012): e32132. (Year: 2012).*

(Continued)

*Primary Examiner* — Benjamin S Melhus
(74) *Attorney, Agent, or Firm* — McDermott Will & Emery LLP

(57) ABSTRACT

A cognitive function evaluation device includes: an obtainment unit configured to obtain speech data indicating speech uttered by a subject; a calculation unit configured to extract a plurality of vowels from the speech data obtained by the obtainment unit, and calculate, for each of the plurality of vowels, a feature value based on a frequency and an amplitude of at least one formant obtained from a spectrum of the vowel; an evaluation unit configured to evaluate a cognitive function of the subject from the feature value calculated by (Continued)

the calculation unit; and an output unit configured to output an evaluation result of the evaluation unit.

10 Claims, 8 Drawing Sheets

(56) References Cited

U.S. PATENT DOCUMENTS

| | | | |
|---|---|---|---|
| 2009/0099848 A1* | 4/2009 | Lerner | G10L 17/26 |
| | | | 704/271 |
| 2012/0053929 A1* | 3/2012 | Hsia | G16H 50/30 |
| | | | 704/9 |
| 2013/0158434 A1* | 6/2013 | Shen | A61B 5/746 |
| | | | 600/586 |
| 2014/0073993 A1* | 3/2014 | Poellabauer | A61B 7/00 |
| | | | 600/586 |
| 2014/0107494 A1 | 4/2014 | Kato et al. | |
| 2015/0112232 A1* | 4/2015 | Quatieri | A61B 5/7264 |
| | | | 600/595 |
| 2017/0053665 A1* | 2/2017 | Quatieri, Jr. | G16H 50/70 |
| 2017/0150907 A1* | 6/2017 | Duffy | A61B 5/7435 |
| 2017/0332935 A1* | 11/2017 | Kraus | A61B 5/0022 |
| 2018/0240535 A1* | 8/2018 | Harper | G16H 50/30 |

FOREIGN PATENT DOCUMENTS

| | | |
|---|---|---|
| JP | 2007-114631 A | 5/2007 |
| JP | 4876207 B2 | 2/2012 |
| WO | 2010/085681 A1 | 7/2010 |
| WO | 2012/165602 A1 | 12/2012 |

OTHER PUBLICATIONS

Yap, Tet Fei, et al. "Cognitive load classification using formant features." 10th International Conference on Information Science, Signal Processing and their Applications (ISSPA 2010). IEEE, 2010. (Year: 2010).*

Machine Translation of JP4876207B2 (Year: 2011).*

M. Charfuelan and G.-J. Kruijff, "Classification of speech under stress and cognitive load in USAR operations," 2013 IEEE International Conference on Acoustics, Speech and Signal Processing, Vancouver, BC, Canada, 2013, pp. 508-512, doi: 10.1109/ICASSP. 2013.6637699. (Year: 2013).*

Search Report dated Jan. 29, 2022 issued in the corresponding Chinese Patent Application No. 201880049623.4, with English translation.

M. Strinzel et al., "Acoustic and Perceptual Correlates of Vowel Articulation in Parkinson's Disease With and Without Mild Cognitive Impairment: A Pilot Study", International Conference on Speech and Computer, 2017, pp. 56-64.

IInternational Search Report issued in corresponding International Patent Application No. PCT/JP2018/027230, dated Aug. 14, 2018, with English translation.

Chinese Office Action issued in corresponding Chinese Patent Application No. 201880049623.4, dated Jul. 22, 2022, with English translation of the Search Report.

* cited by examiner

|  | NORMAL CONTROLS (NC) | MILD COGNITIVE IMPAIRMENT (MCI) | ALZHEIMER'S DISEASE (AD) |
|---|---|---|---|
| NUMBER OF SUBJECTS | 90 | 94 | 93 |
| MoCA AVERAGE SCORE | 27.4 | 22.1 | 16.2 |
| MoCA SCORE RANGE | 25.2 - 29.6 | 19.0 - 25.2 | 11.4 - 21.0 |

COGNITIVE FUNCTION EVALUATION DEVICE, COGNITIVE FUNCTION EVALUATION SYSTEM, AND COGNITIVE FUNCTION EVALUATION METHOD

CROSS-REFERENCE OF RELATED APPLICATIONS

This application is the U.S. National Phase under 35 U.S.C. § 371 of International Patent Application No. PCT/JP2018/027230, filed on Jul. 20, 2018, which in turn claims the benefit of Japanese Patent Application No. 2017-163795, filed on Aug. 28, 2017, the entire disclosures of which Applications are incorporated by reference herein.

TECHNICAL FIELD

The present invention relates to a cognitive function evaluation device, a cognitive function evaluation system, and a cognitive function evaluation method that can evaluate a cognitive function of a subject.

BACKGROUND ART

As cognitive function evaluation tests, methods by which a subject, i.e. a patient whose cognitive function is to be evaluated, writes answers on test paper are conventionally available. The methods include Hasegawa's Dementia Scale-Revised (HDS-R), Mini-Mental State Examination (MMSE), and Clinical Dementia Rating (CDR). These tests are conducted on the subject by a doctor, a clinical psychologist, or the like with certain training, in a medical institution.

Such evaluation methods using test paper have a problem of imposing a burden on the subject as it requires a long test time. There is also a problem in that, in the case where the test is repeatedly conducted on the subject, the subject may memorize the answers because the test is the same. To solve the problems, a technique by which a doctor or the like sound-records questions and answers in a test conducted on a subject and analyzes speech of the subject is disclosed (for example, see PTL 1).

CITATION LIST

Patent Literature

PTL 1: Japanese Patent No. 4876207

SUMMARY OF THE INVENTION

Technical Problem

For cognitive function evaluation, a cognitive function of a subject needs to be evaluated more easily and accurately.

The present invention therefore has an object of providing a cognitive function evaluation device, etc. that can evaluate a cognitive function of a subject easily and accurately.

Solutions to Problem

A cognitive function evaluation device according to an aspect of the present invention includes: an obtainment unit configured to obtain speech data indicating speech uttered by a subject; a calculation unit configured to extract a plurality of vowels from the speech data obtained by the obtainment unit, and calculate, for each of the plurality of vowels, a feature value based on a frequency and an amplitude of at least one formant obtained from a spectrum of the vowel; an evaluation unit configured to evaluate a cognitive function of the subject from the feature value calculated by the calculation unit; and an output unit configured to output an evaluation result of the evaluation unit.

A cognitive function evaluation system according to an aspect of the present invention includes: the foregoing cognitive function evaluation device; a sound collection device that detects the speech of the subject; and a display device that displays the evaluation result output from the output unit.

A cognitive function evaluation method according to an aspect of the present invention includes: obtaining speech data indicating speech uttered by a subject; extracting a plurality of vowels from the speech data obtained in the obtaining, and calculating, for each of the plurality of vowels, a feature value based on a frequency and an amplitude of at least one formant obtained from a spectrum of the vowel; and evaluating a cognitive function of the subject from the feature value calculated in the calculating, and outputting an evaluation result.

The present invention may be implemented as a non-transitory computer-readable recording medium having recorded thereon a program for causing a computer to execute steps included in the cognitive function evaluation method.

Advantageous Effect of Invention

A cognitive function evaluation device, etc. according to an aspect of the present invention can evaluate a cognitive function of a subject easily and accurately.

DESCRIPTION OF EXEMPLARY EMBODIMENT

An embodiment will be described below, with reference to drawings. The embodiment described below shows a general or specific example. The numerical values, shapes, materials, structural elements, the arrangement and connection of the structural elements, steps, the processing order of the steps etc. shown in the following embodiment are mere examples, and do not limit the scope of the present invention. Of the structural elements in the embodiment described below, the structural elements not recited in any one of the independent claims representing the broadest concepts are described as optional structural elements.

Each drawing is a schematic and does not necessarily provide precise depiction. The substantially same structural elements are given the same reference marks throughout the drawings, and repeated description may be omitted or simplified.

Expressions indicating directions are used in the following embodiment. For example, "parallel" denotes not only perfectly parallel but also substantially parallel, that is, allows for a deviation of about several %, for example.

Embodiment

[Structure of Cognitive Function Evaluation Device]

Figure 1:
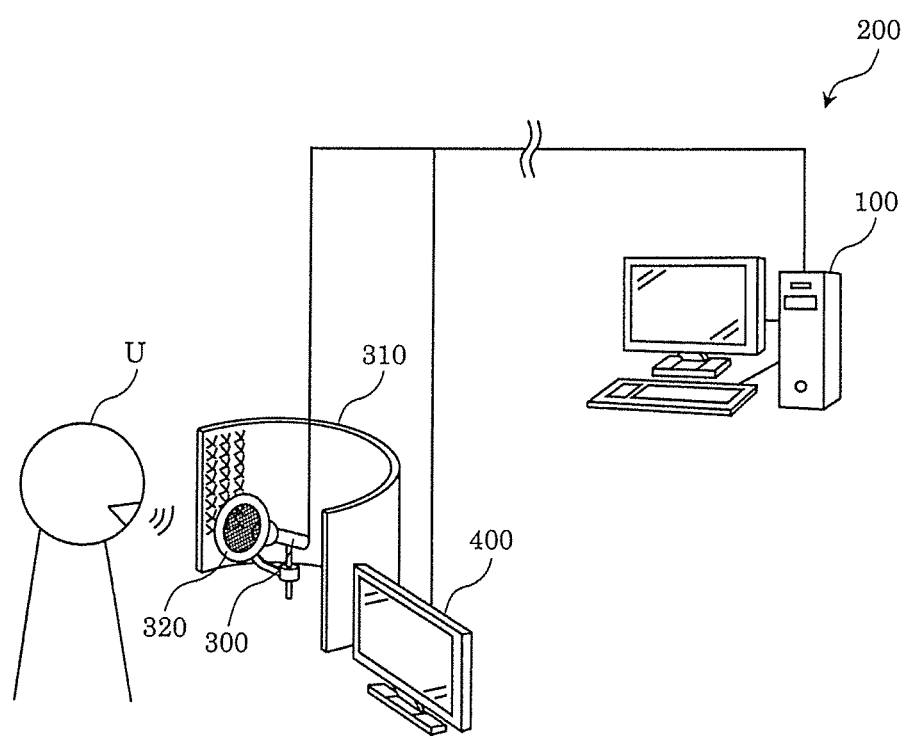
FIG. 1 is a diagram illustrating a structure of a cognitive function evaluation system according to an embodiment.

A structure of a cognitive function evaluation system according to an embodiment will be described below. FIG. 1 is a diagram illustrating the structure of the cognitive function evaluation system according to the embodiment.

Cognitive function evaluation system 200 is an apparatus for evaluating a cognitive function of subject U from speech of subject U. The cognitive function indicates the ability to recognize, remember, and judge. As a specific example, cognitive function evaluation device 100 evaluates whether a person has dementia (dementia patient).

Dementia has symptoms of a decline in the foregoing cognitive function. A specific example of dementia is Alzheimer's dementia (AD: Alzheimer's disease). Since dementia has no subjective symptoms, a family member of a dementia patient, a third party, or the like urges the dementia patient to go to hospital, and accordingly the dementia patient seeks medical attention. As a result of subject U taking a batch test for diagnosis of dementia such as the Montreal Cognitive Assessment (MoCA) test, whether subject U has dementia can be determined.

However, the MoCA test takes about 15 minutes. Moreover, for diagnosis of changes of subject U over time, the MoCA test needs to be conducted a plurality of times at intervals of one or more days, to determine whether subject U has dementia. Thus, the MoCA test requires a long time to diagnose whether subject U has dementia.

It is known that a dementia patient and a person without dementia (healthy subject) differ in speech even when they utter the same word.

Cognitive function evaluation system 200 is an apparatus that accurately evaluates the cognitive function of subject U by analyzing speech of subject U.

Cognitive function evaluation system 200 includes cognitive function evaluation device 100, sound collection device 300, and display device 400, as illustrated in FIG. 1.

Cognitive function evaluation device 100 is a computer that obtains, through sound collection device 300, speech data indicating speech uttered by subject U and evaluates the cognitive function of subject U from the obtained speech data.

Sound collection device 300 is a microphone that detects speech uttered by subject U and outputs speech data indicating the detected speech to cognitive function evaluation device 100. For accurate detection of speech uttered by subject U, sound barrier 310 and/or pop filter 320 may be provided around sound collection device 300.

Display device 400 displays an image based on image data output from cognitive function evaluation device 100. Specifically, display device 400 is a monitor device composed of a liquid crystal panel, an organic EL panel, or the like. Display device 400 may be an information terminal such as a television, a smartphone, or a tablet terminal.

Cognitive function evaluation device 100, sound collection device 300, and display device 400 are capable of transmission/reception of speech data or image data with each other, and may be connected by wire or connected to enable wireless communication.

Cognitive function evaluation device 100 analyzes speech of subject U based on speech data detected by sound collection device 300, evaluates the cognitive function of subject U from the analysis result, and outputs an image indicating the evaluation result to display device 400. Thus, cognitive function evaluation device 100 can notify the degree of the cognitive function to the dementia patient who has no subjective symptoms, and can, for example, urge the dementia patient to seek medical attention. In other words, by notifying the degree of the cognitive function to the dementia patient who has no subjective symptoms, cognitive function evaluation device 100 can aid the dementia patient in seeking medical attention.

Cognitive function evaluation device 100 is, for example, a personal computer. Alternatively, cognitive function evaluation device 100 may be a server device.

Figure 2:
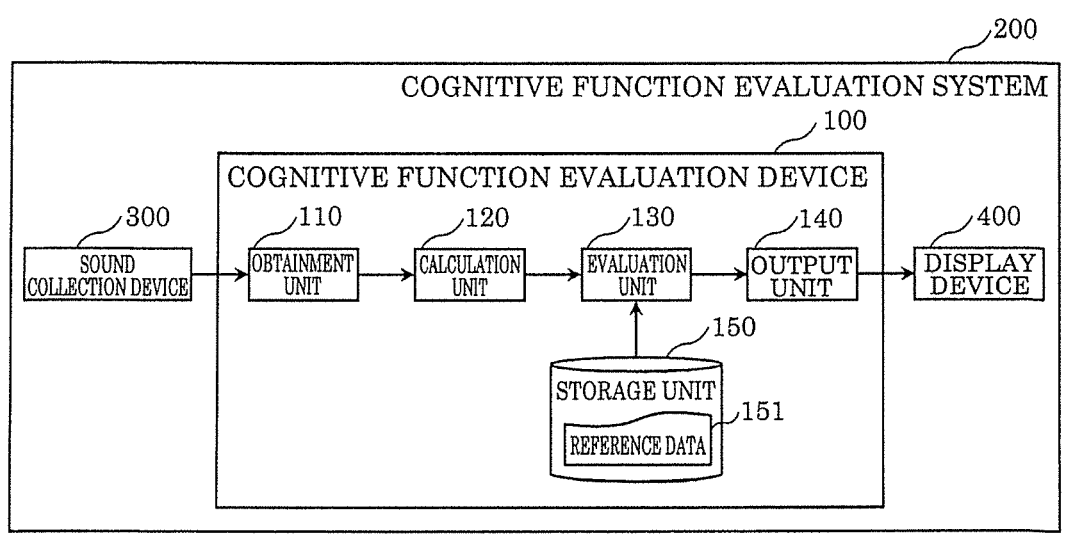
FIG. 2 is a block diagram illustrating a characteristic functional structure of the cognitive function evaluation system according to the embodiment.

FIG. 2 is a block diagram illustrating a characteristic functional structure of cognitive function evaluation device 100 according to the embodiment. Cognitive function evaluation device 100 includes obtainment unit 110, calculation unit 120, evaluation unit 130, output unit 140, and storage unit 150.

Obtainment unit 110 obtains speech data detected by sound collection device 300. Obtainment unit 110 is, for example, a communication interface for performing wire communication or wireless communication.

Calculation unit 120 is a processing unit that analyzes the speech data of subject U obtained by obtainment unit 110. Specifically, calculation unit 120 is implemented by a processor, a microcomputer, or a dedicated circuit.

Calculation unit 120 extracts a plurality of vowels from the speech data obtained by obtainment unit 110, and, for each of the plurality of vowels, calculates a feature value based on the frequency and amplitude of at least one formant obtained from the spectrum of the vowel. Herein, the feature value is a numeric value indicating the feature of the speech of subject U calculated from the speech data and used by evaluation unit 130 to evaluate the cognitive function of subject U. For example, the feature value is the frequency and amplitude of the second formant. Calculation unit 120 calculates, for example, the frequency and amplitude of the second formant as the feature value, for each of the plurality of vowels.

The feature value calculated by calculation unit 120 is not limited to the frequency and amplitude of the second formant. For example, calculation unit 120 may calculate the spectrum of each vowel extracted from the speech data obtained by obtainment unit 110, calculate the frequencies and amplitudes of a plurality of the second formants at predetermined time intervals in the calculated spectrum of the vowel, and calculate, from the calculated frequencies and amplitudes of the plurality of the second formants, the standard deviation of the frequencies and amplitudes of the plurality of the second formants as the feature value.

Calculation unit 120 may calculate the spectrum of each vowel extracted from the speech data obtained by obtainment unit 110, calculate the frequencies and amplitudes of a plurality of the second formants at predetermined time intervals in the calculated spectrum of the vowel, and calculate the amount of change of the calculated frequencies and amplitudes of the plurality of the second formants with time as the feature value.

Calculation unit 120 may calculate the spectrum of each of the plurality of vowels extracted from the speech data obtained by obtainment unit 110, calculate, from the calculated spectrum of the vowel, the frequency and amplitude of the first formant and the frequency and amplitude of the second formant, and calculate the calculated frequency of the second formant relative to the calculated frequency of the first formant and the calculated amplitude of the second formant relative to the calculated amplitude of the first formant as the feature value.

The frequency of the second formant is the peak frequency of amplitude that appears second from the low frequency side of human speech, and is known to tend to reflect influence relating to the position of the tongue among resonance generated by vocal sound source in the vocal tract such as the oral cavity, e.g. the lips or the tongue, or the nasal cavity. A dementia patient tends to have poorer motor function of maintaining the position of the tongue or the jaws than a healthy subject. Hence, the frequency and amplitude of the second formant are likely to be different between a healthy subject and a dementia patient. By using a value relating to the frequency and amplitude of the second formant as the feature value for cognitive function evaluation, the cognitive function of subject U can be evaluated more accurately.

The frequency of the first formant is the peak frequency of amplitude that appears first from the low frequency side of human speech, and is known to tend to reflect feature relating to the movement of the tongue. A dementia patient tends to have poorer movement of the tongue than a healthy subject. Hence, the frequency of the first formant is likely to be different between a healthy subject and a dementia patient. By using a value relating to the frequency and amplitude of the first formant as the feature value for cognitive function evaluation together with the frequency and amplitude of the second formant, the cognitive function of subject U can be evaluated further accurately.

Calculation unit 120 may calculate at least one of a time from when output unit 140 outputs task information to when obtainment unit 110 obtains speech data, a temporal change of amplitude of speech, and whether an answer to the task information is correct, as the feature value. The task information herein is information including information of text that is displayed by display device 400 and to be uttered by subject U. Examples of the text included in the task information include text to be read out by subject U such as a tongue twister or one or more randomly displayed vowels, e.g. "e", "o e u", or "i a e o", and text for testing memory of subject U such as prefecture names.

Evaluation unit 130 checks the feature value calculated by calculation unit 120 against reference data 151 stored in storage unit 150, and evaluates the cognitive function of subject U. Specifically, evaluation unit 130 is implemented by a processor, a microcomputer, or a dedicated circuit. Calculation unit 120 and evaluation unit 130 may be implemented by one processor, microcomputer, or dedicated circuit having the functions of both units, or implemented by a combination of two or more processors, microcomputers, or dedicated circuits.

Output unit 140 outputs the evaluation result of the cognitive function of subject U by evaluation unit 130 to display device 400. Output unit 140 is, for example, a communication interface for performing wire communication or wireless communication.

Storage unit 150 is a storage device that stores reference data 151 indicating the relationship between the feature value and the human cognitive function. Reference data 151 is referenced by evaluation unit 130 when evaluating the degree of the cognitive function of subject U. Storage unit 150 is implemented, for example, by read only memory (ROM), random access memory (RAM), semiconductor memory, or a hard disk drive (HDD).

Storage unit 150 also stores a program executed by calculation unit 120 and evaluation unit 130, and image data that is used when outputting the evaluation result of the cognitive function of subject U and indicates the evaluation result.

[Procedure of Cognitive Function Evaluation Method]

A specific procedure of a cognitive function evaluation method performed by cognitive function evaluation device 100 will be described below.

Obtainment unit 110 obtains speech data of subject U through sound collection device 300 (Step S101). In Step S101, for example, subject U utters a word, such as "arigatou" ("thank you" in Japanese), containing a plurality of vowels from among "a", "i", "u", "e", and "o", to sound collection device 300. Obtainment unit 110 obtains speech such as "arigatou" uttered by subject U as speech data, through sound collection device 300.

Next, calculation unit 120 extracts the plurality of vowels from the speech data obtained by obtainment unit 110 (Step S102). In Step S102, for example, calculation unit 120 extracts the vowels "a" and "u" from the speech data such as "arigatou" obtained by obtainment unit 110 in Step S101.

Calculation unit 120 then calculates, from each of the plurality of vowels extracted in Step S102, the spectrum of the vowel, and calculates a feature value based on the frequency and amplitude of at least one formant of the vowel from the calculated spectrum of the vowel (Step S103). In Step S103, for example, calculation unit 120 calculates, from the spectrum of each of the plurality of vowels calculated in Step S102, the frequency and amplitude of the first formant which is the formant lowest in frequency and the frequency and amplitude of the second formant which is the formant next lowest in frequency after the first formant. In Step S103, calculation unit 120 may calculate the frequency and amplitude of the third formant, the frequency and amplitude of the fourth formant, etc.

Next, evaluation unit 130 evaluates the cognitive function of subject U from the frequency and amplitude of the formant in each of the plurality of vowels calculated by calculation unit 120 in Step S103 (Step S104). In Step S104, for example, evaluation unit 130 evaluates the cognitive function of subject U, from the feature value based on the frequency and amplitude of the formant in each of the plurality of vowels calculated by calculation unit 120 in Step S103 and reference data 151 stored in storage unit 150.

Next, output unit 140 outputs the evaluation result of the cognitive function of subject U by evaluation unit 130 (Step S105). In Step S105, for example, output unit 140 obtains an image corresponding to the evaluation result of evaluation unit 130 in Step S104 from storage unit 150, and transmits the obtained image to display device 400.

Display device 400 obtains the image output from output unit 140, and displays the image. This allows subject U to see the cognitive function evaluation result easily.

Figure 3:
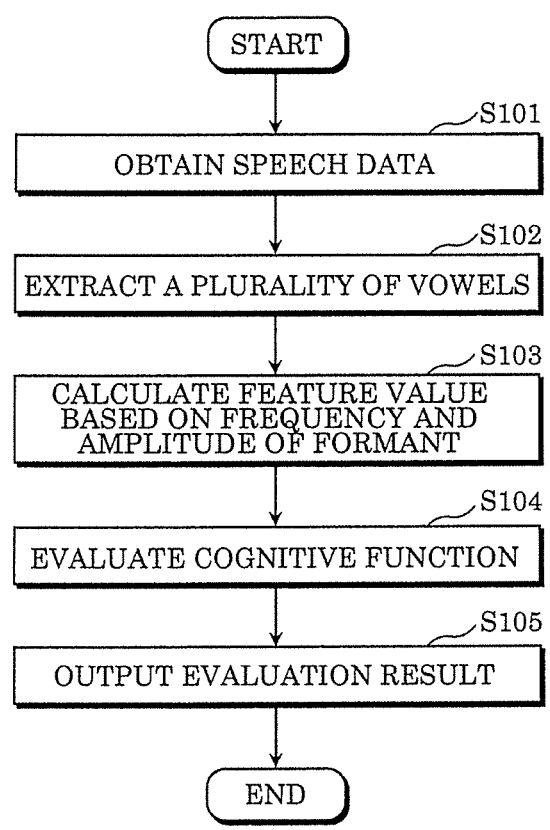
FIG. 3 is a flowchart illustrating a procedure by which a cognitive function evaluation device according to the embodiment evaluates a cognitive function of a subject.
Figure 4:
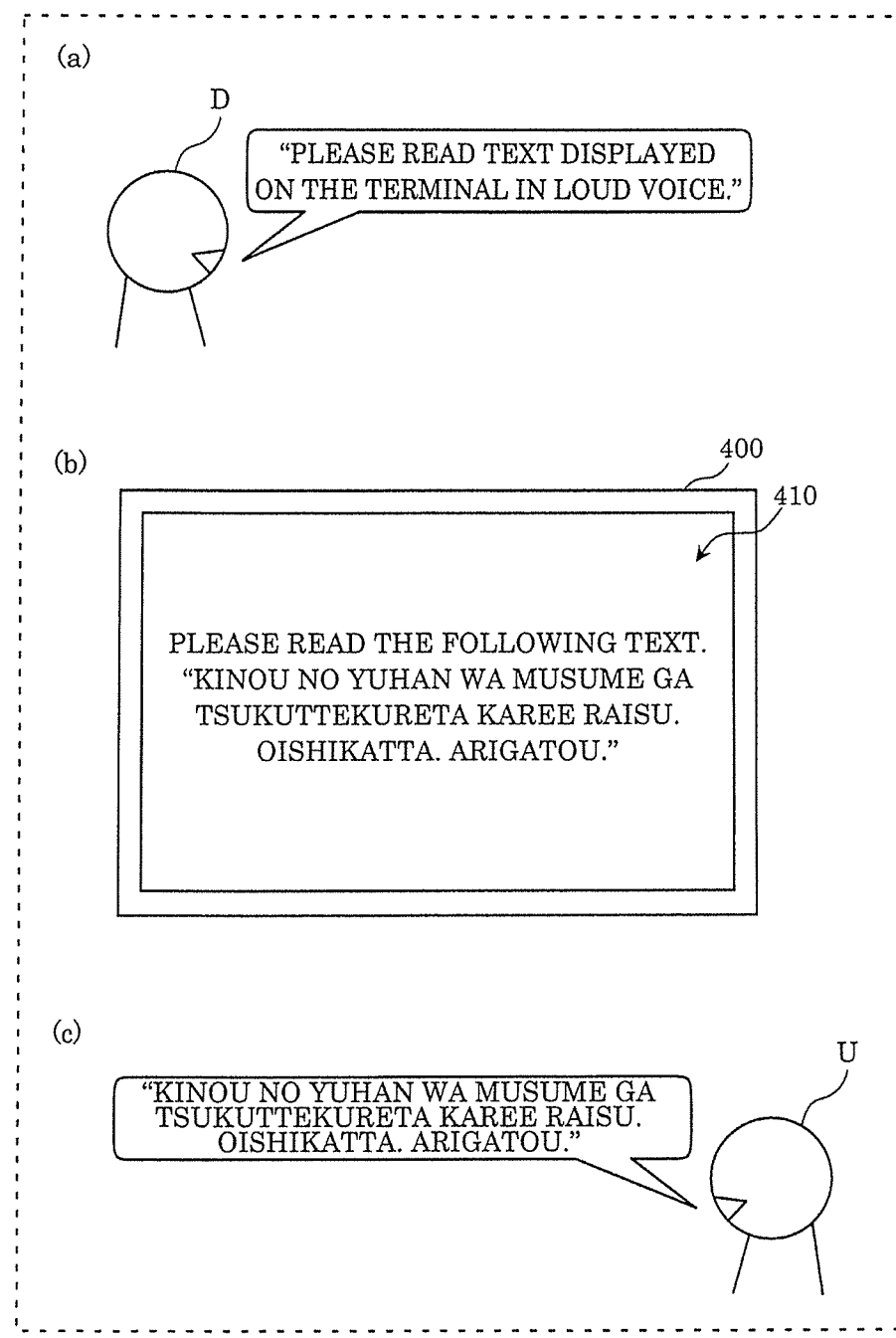
FIG. 4 is a diagram illustrating an example of a method by which an obtainment unit obtains speech data of the subject.

FIG. 4 is a diagram illustrating an example of a method by which obtainment unit 110 obtains speech data of subject U in Step S101 in FIG. 3.

As illustrated in (a) in FIG. 4, doctor D or the like asks subject U: "Please read text displayed on the terminal in loud voice." Doctor D may directly talk to subject U, the recorded speech may be played to subject U, or the explanation may be displayed by display device 400. By playing the recorded speech to subject U or displaying the explanation by display device 400, subject U can check his or her cognitive function using cognitive function evaluation device 100 even when doctor D is not present near subject U.

Next, as illustrated in (b) in FIG. 4, image 410 including text that is task information to be uttered by subject U is displayed by display device 400. The text included in image 410 is not limited as long as it contains a plurality of vowels. Image 410 including text "Kinou no yuhan wa musume ga tsukuttekureta karee raisu. Oishikatta. Arigatou." ("Last night's dinner was curry and rice made by my daughter. It was delicious. Thank you." in Japanese) is illustrated in (b) in FIG. 4. The text included in image 410 may or may not contain letters other than vowels. The text included in image 410 may be a word (or words).

Next, as illustrated in (c) in FIG. 4, subject U utters the text included in image 410. In FIG. 4, calculation unit 120 extracts, for example, "a" and "u" of "arigatou".

By displaying the text to be uttered by subject U in image 410, noise is reduced when detecting the speech of subject U, as compared with the case where doctor D says the text to subject U.

The time from when the text to be uttered by subject U is presented to subject U to when subject U utters the text may be measured and used for cognitive function evaluation. In this case, calculation unit 120 calculates the time from when output unit 140 outputs the task information (specifically, image 410 illustrated in (b) in FIG. 4) to when obtainment unit 110 obtains the speech data, as a feature value. By displaying the text to be uttered by subject U in image 410, the time from when the text to be uttered by subject U is presented to subject U to when subject U utters the text is measured accurately, as compared with the case where doctor D says the text to subject U.

Figure 5:
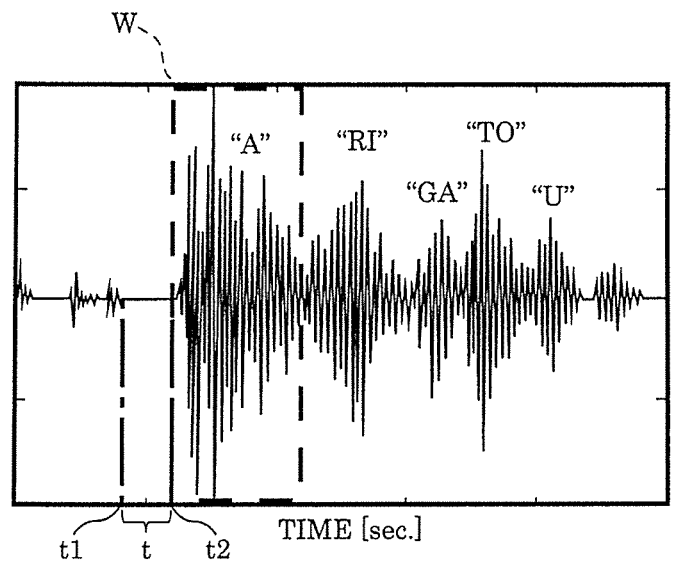
FIG. 5 is a diagram illustrating an example of speech data indicating speech uttered by the subject.

FIG. 5 is a diagram illustrating an example of speech data indicating speech uttered by subject U. Specifically, FIG. 5 is a graph indicating speech data in the case where subject U utters "arigatou". In the graph in FIG. 5, the horizontal axis represents time, and the vertical axis represents amplitude.

As illustrated in FIG. 5, the graph shows changes in sound pressure corresponding to "a", "ri", "ga", "to", and "u". In Step S101 (see FIG. 3), obtainment unit 110 obtains the data illustrated in FIG. 5 from subject U as speech data. In Step S102 (see FIG. 3), for example, calculation unit 120 extracts the vowels "a" and "u" from the speech data illustrated in FIG. 5 by a known method. More specifically, in Step S102 (see FIG. 3), calculation unit 120 extracts extraction range W of speech data indicating the vowel "a" from the speech data illustrated in FIG. 5 by a known method.

Elapsed time t from when the text to be uttered by subject U is presented to subject U to when subject U utters the text may be measured and used for cognitive function evaluation. In this case, calculation unit 120 calculates elapsed time t, from display time t1 which is the time at which output unit 140 outputs the task information and utterance time t2 which is the time at which obtainment unit 110 obtains the speech data. There is likely a time difference between the time at which output unit 140 outputs the task information and the time at which display device 400 displays the task information. In such a case, display time t1 may be any of the time at which output unit 140 outputs the task information and the time at which display device 400 displays the task information. In the case where the time difference is known beforehand, display time t1 may be the time obtained by correcting the time at which output unit 140 outputs the task information by the time difference.

To measure time, cognitive function evaluation device 100 may include a clocking unit such as a real time clock (RTC).

Figure 6:
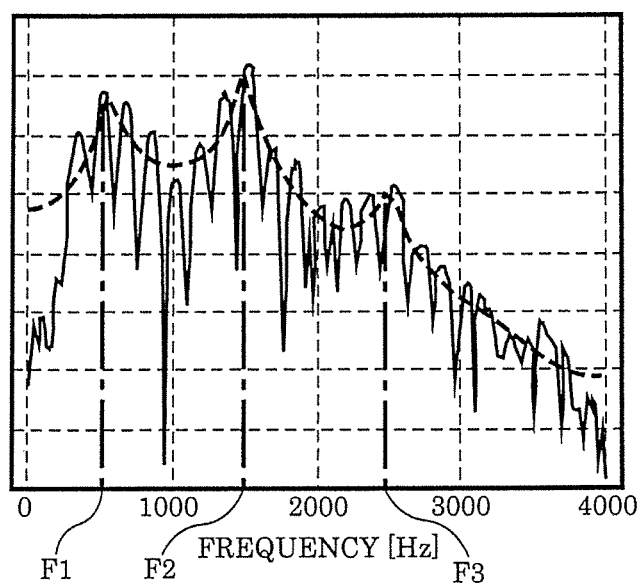
FIG. 6 is an explanatory diagram illustrating frequencies of formants calculated by a calculation unit from speech data.

FIG. 6 is an explanatory diagram illustrating frequencies of formants calculated by calculation unit 120 from speech data. Specifically, FIG. 6 is a graph indicating the spectrum of the vowel obtained by converting the horizontal axis of the speech data illustrated in FIG. 5 into frequency. The vertical axis in FIG. 6 represents amplitude.

As indicated by dashed lines in FIG. 6, the data obtained by converting the horizontal axis of the speech data into frequency has a plurality of peaks. Of the plurality of peaks, the frequency of the peak lowest in frequency is frequency F1 of the first formant. The frequency of the peak next lowest in frequency after frequency F1 of the first formant is frequency F2 of the second formant. The frequency of the peak next lowest in frequency after frequency F2 of the second formant is frequency F3 of the third formant. Thus, calculation unit 120 extracts the vowel part from the speech data obtained by obtainment unit 110 by a known method, calculates the spectrum of the vowel by data conversion of the speech data of the extracted vowel part into amplitude against frequency, and calculates the frequencies of the formants. The "amplitude of the formant" is, for example, the peak intensity at the frequency of each formant in FIG. 6.

The graph illustrated in FIG. 6 is calculated by subjecting the speech data illustrated in FIG. 5 to regression analysis. Examples of the regression analysis include cepstrum analysis and linear predictive analysis (linear predictive coding: LPC).

Figures 7, 8:
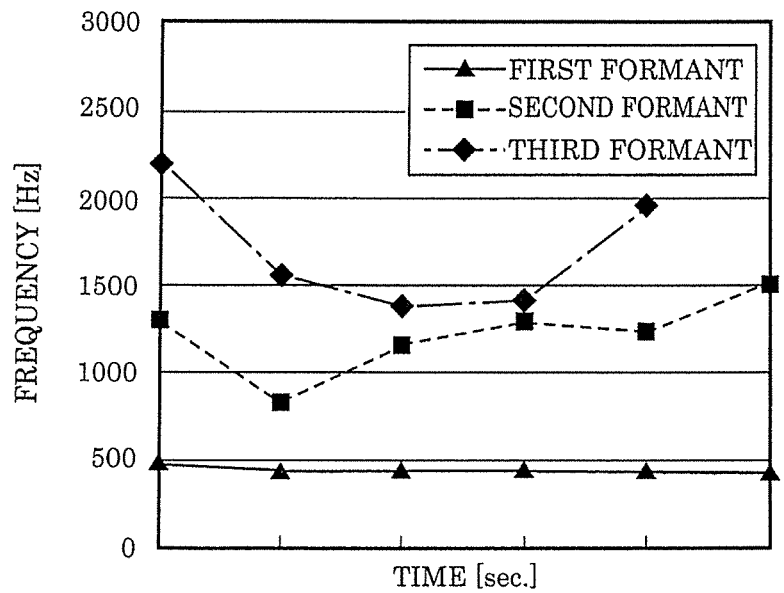
FIG. 7 is a diagram illustrating an example of temporal changes in frequencies of formants calculated by the calculation unit from speech data.
FIG. 8 is a diagram illustrating scores earned by subjects in the MoCA test.

FIG. 7 is a diagram illustrating an example of temporal changes in frequencies of formants calculated by calculation unit 120 from speech data. Specifically, FIG. 7 is a graph illustrating an example of temporal changes in frequency F1 of the first formant, frequency F2 of the second formant, and frequency F3 of the third formant.

For example, subject U utters a vowel such as "a" for several seconds. Cognitive function evaluation device 100 divides the speech uttered by subject U at predetermined time intervals such as 60 msec, and calculates the frequency of the formant in each time interval. In this way, calculation unit 120 calculates the amount of change of the frequency of the formant with time, the standard deviation of the frequency of the formant, or the like. The predetermined time intervals may be set freely. For example, the predetermined time intervals may be less than 60 msec, or more than 60 msec. The time width when calculating the standard deviation may be set freely. When calculating the frequency of the formant, the temporal change of the amplitude of the formant may be calculated as well.

In diagnosis of dementia, whether subject U has dementia can be determined as a result of subject U taking the MoCA test which is a batch test for diagnosis of dementia. FIG. 8 is a diagram illustrating scores earned by subjects U in the MoCA test.

The present inventors conducted the MoCA test on a plurality of subjects including healthy subjects (NC: normal control), mild dementia patients (MCI: mild cognitive impairment), and dementia patients (AD). The number of subjects of NC was 90, the number of subjects of MCI was 94, and the number of subjects of AD was 93.

As illustrated in FIG. 8, the average score of MoCA (MoCA average score) and the score range of MoCA (MoCA score range) were different among NC, MCI, and AD. Specifically, the MoCA average score of NC was 27.4, the MoCA average score of MCI was 22.1, and the MoCA average score of AD was 16.2. By using, as reference data 151, the correlation between the results of the MoCA test and the like obtained in this way and the feature values of subjects U such as frequency F1 of the first formant and frequency F2 of the second formant, cognitive function evaluation device 100 can evaluate the cognitive function of subject U from speech of subject U and reference data 151.

Figure 9:
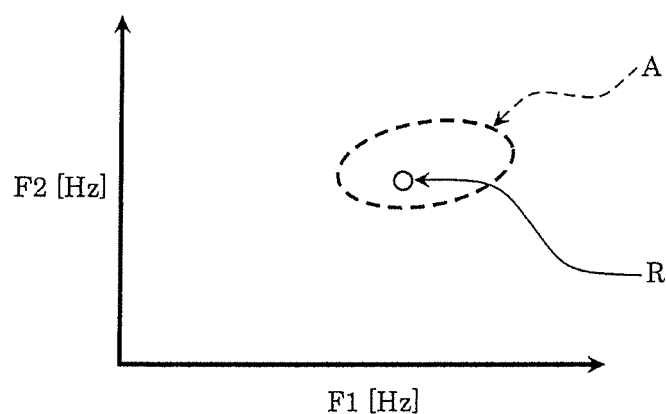
FIG. 9 is an explanatory diagram illustrating an example of the relationship between reference data and a feature value of speech data calculated by the calculation unit.

FIG. 9 is an explanatory diagram illustrating an example of the relationship between reference data 151 and a feature value of speech data calculated by calculation unit 120.

For example, storage unit 150 stores data indicating which of NC, MCI, and AD corresponds, as cognitive function, to the ratio of frequency F1 of the first formant and frequency F2 of the second formant, as reference data 151. In the example in FIG. 9, in the case where the ratio of frequency F1 of the first formant and frequency F2 of the second formant as the feature value of subject U is within range A indicated by a dashed line in the graph, evaluation unit 130 evaluates subject U as MCI. For example, in the case where the feature value of subject U calculated by calculation unit 120 is feature value R in FIG. 9, evaluation unit 130 determines whether feature value R is within range A, and, if feature value R is within range A, determines the cognitive function of subject U as MCI.

Figure 10:
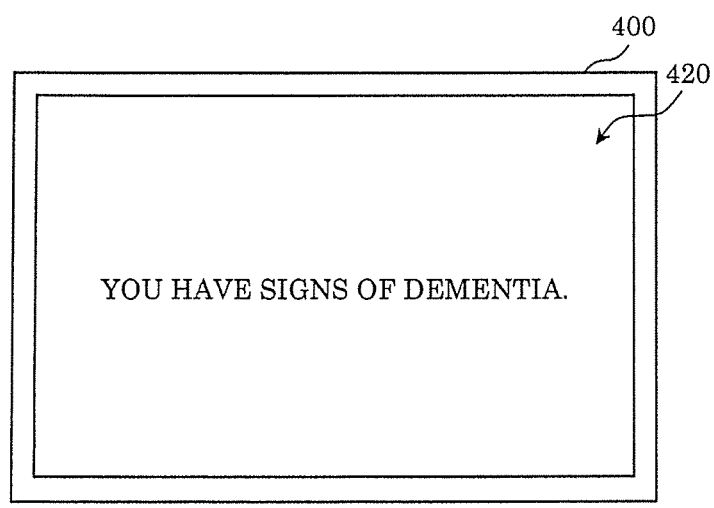
FIG. 10 is a diagram illustrating an example of an image that is displayed by a display device to indicate a decrease in cognitive function.

FIG. 10 is a diagram illustrating an example of an image that is displayed by display device 400 to indicate a decrease in cognitive function.

Display device 400 displays image 420 illustrated in FIG. 10, as the evaluation result of evaluation unit 130. Image 420 is an example of an image displayed in the case where evaluation unit 130 evaluates the cognitive function of subject U as MCI. Display device 400 displays the evaluation result of evaluation unit 130 as an image in this way. For example, in the case where subject U evaluates his or her cognitive function using cognitive function evaluation device 100 at home, cognitive function evaluation device 100 can urge subject U to seek medical attention.

[Effects, Etc.]

Cognitive function evaluation device 100 according to the embodiment includes obtainment unit 110, calculation unit 120, evaluation unit 130, and output unit 140. Obtainment unit 110 obtains speech data indicating speech uttered by subject U. Calculation unit 120 extracts a plurality of vowels from the speech data obtained by obtainment unit 110, and calculates, for each of the plurality of vowels, a feature value based on a frequency and amplitude of at least one formant obtained from a spectrum of the vowel. Evaluation unit 130 evaluates a cognitive function of subject U from the feature value calculated by calculation unit 120. Output unit 140 outputs an evaluation result of evaluation unit 130.

Thus, cognitive function evaluation device 100 calculates, from the speech data of the speech uttered by subject U, the frequency and amplitude of the formant as the feature value. The frequency and amplitude of the formant are likely to differ in feature among NC, MCI, and AD. Hence, with cognitive function evaluation device 100, the cognitive function of subject U can be evaluated easily and accurately, with no need for analysis and storage of a large amount of data through machine learning and the like. Moreover, by subjecting the plurality of vowels to evaluation, the cognitive function of subject U can be evaluated more accurately.

For example, calculation unit 120 may calculate frequency F2 and amplitude of a second formant as the feature value, as the frequency and amplitude of the at least one formant.

Frequency F2 of the second formant is the peak frequency of amplitude that appears second from the low frequency side of human speech, and is known to tend to reflect influence relating to the position of the tongue among resonance generated by vocal sound source in the vocal tract such as the oral cavity, e.g. the lips or the tongue, or the nasal cavity. For example, AD tends to have poorer motor function of maintaining the position of the tongue or the jaws. Hence, frequency F2 and amplitude of the second formant are likely to be different between NC and AD. By using a value relating to frequency F2 and amplitude of the second formant as the feature value for cognitive function evaluation, the cognitive function of subject U can be evaluated more accurately.

For example, calculation unit 120 may calculate, as the frequency of the at least one formant, frequencies F2 and amplitudes of a plurality of second formants at predetermined time intervals in the spectrum calculated from the speech data, and calculate, from calculated frequencies F2 and amplitudes of the plurality of second formants, a standard deviation of frequencies F2 and amplitudes of the plurality of second formants as the feature value.

For example, AD tends to have poorer motor function of maintaining the position of the tongue or the jaws, as mentioned above. Accordingly, AD tends to utter unstable speech, as compared with NC. Since speech uttered by AD tends to vary as compared with NC, the standard deviation of frequency F2 and amplitude of the second formant is likely to be large. By using the standard deviation of frequency F2 and amplitude of the second formant as the feature value for cognitive function evaluation, the cognitive function of subject U can be evaluated more accurately.

For example, calculation unit 120 may calculate, as the frequency of the at least one formant, frequencies F2 and amplitudes of a plurality of second formants at predetermined time intervals in the spectrum calculated from the speech data, and calculate an amount of change of calculated frequencies F2 and amplitudes of the plurality of second formants with time as the feature value.

For example, AD tends to have poorer motor function of maintaining the position of the tongue or the jaws, as mentioned above. Accordingly, AD tends to utter unstable speech, as compared with NC. Since speech uttered by AD tends to vary as compared with NC, the temporal change of frequency F2 and amplitude of the second formant is likely to be large. By using the amount of change of frequency F2 and amplitude of the second formant with time as the feature value for cognitive function evaluation, the cognitive function of subject U can be evaluated more accurately.

For example, calculation unit 120 may calculate, as the frequency and amplitude of the at least one formant, frequency F1 and amplitude of the first formant and frequency F2 and amplitude of the second formant from the spectrum calculated from the speech data. Calculation unit 120 may further calculate frequency F2 of the second formant relative to frequency F1 of the first formant and the amplitude of the second formant relative to the amplitude of the first formant, as the feature value.

Frequency F1 of the first formant is the peak frequency of amplitude that appears first from the low frequency side of human speech, and is known to tend to reflect feature relating to the movement of the tongue. AD tends to have poorer movement of the tongue than NC. Hence, frequency F1 and amplitude of the first formant are likely to be different between NC and AD. Moreover, the frequency and amplitude of a formant are expected to differ among individuals. Furthermore, frequency F1 and amplitude of the first formant and frequency F2 and amplitude of the second formant are expected to correlate with each other, for each individual. By using frequency F2 of the second formant relative to frequency F1 of the first formant and the amplitude of the second formant relative to the amplitude of the first formant as the feature value for cognitive function evaluation, the cognitive function of subject U can be evaluated further accurately while reducing individual differences.

For example, cognitive function evaluation device 100 may further include storage unit 150 that stores reference data 151 indicating a relationship between information about a feature value of a person and a cognitive function of the person. Evaluation unit 130 may check the feature value of subject U against reference data 151 stored in storage unit 150, to evaluate the cognitive function of subject U.

Thus, cognitive function evaluation device 100 calculates the feature value based on the frequency and amplitude of the formant from the obtained speech data, and checks the calculated feature value against reference data 151, thus evaluating the cognitive function of subject U. Hence, with cognitive function evaluation device 100, the cognitive function of subject U can be evaluated easily and accurately, with no need for analysis and storage of a large amount of data through machine learning and the like.

For example, output unit 140 may output task information for causing subject U to utter specific speech. Calculation unit 120 may further calculate at least one of: a time from when output unit 140 outputs the task information to when obtainment unit 110 obtains the speech data; a temporal change of amplitude indicated by the speech data; and whether an answer to the task information is correct, as the feature value.

AD tends to have lower reaction speed than NC. Accordingly, the time from when the task information is presented by display device 400 to when subject U utters the speech is likely to be different between NC and AD. By further using the time from when the task information is displayed by display device 400 to when subject U utters the speech as the feature value for cognitive function evaluation, the cognitive function of subject U can be evaluated further accurately.

AD tends to have poorer movement of the muscles around the mouth such as the tongue and the jaws, than NC. Hence, AD is likely to be unstable in amplitude, as compared with NC. By using the temporal change of the amplitude of the subject as the feature value for cognitive function evaluation together with the frequency of the formant, the cognitive function of subject U can be evaluated further accurately.

AD also has a high possibility of answering even a simple question wrong, as compared with NC. By forming text included in the task information as a question having a correct answer (quiz) and further using information of whether an answer is correct as the feature value for cognitive function evaluation, the cognitive function of subject U can be evaluated further accurately.

Cognitive function evaluation system 200 according to the embodiment includes: cognitive function evaluation device 100; sound collection device 300 that detects the speech of the subject and outputs the speech data indicating the detected speech to obtainment unit 110; and display device 400 that displays the evaluation result output from output unit 140.

Thus, cognitive function evaluation system 200 can detect the speech of subject U by sound collection device 300, evaluate the cognitive function of subject U by cognitive function evaluation device 100, and display the evaluation result by display device 400. Hence, with cognitive function evaluation system 200, the cognitive function of subject U can be evaluated easily and accurately, with no need for analysis and storage of a large amount of data through machine learning and the like.

A cognitive function evaluation method according to the embodiment includes: obtaining speech data indicating speech uttered by subject U; extracting a plurality of vowels from the obtained speech data, and calculating, for each of the plurality of vowels, a feature value based on a frequency and amplitude of at least one formant obtained from a spectrum of the vowel; and evaluating a cognitive function of the subject from the calculated feature value, and outputting an evaluation result.

Thus, the cognitive function evaluation method according to the embodiment calculates, from the speech data of the speech uttered by subject U, the frequency and amplitude of the formant as the feature value. The frequency and amplitude of the formant are likely to differ in feature among NC, MCI, and AD. Hence, with the cognitive function evaluation method according to the embodiment, the cognitive function of subject U can be evaluated easily and accurately, with no need for analysis and storage of a large amount of data through machine learning and the like.

The present invention may be implemented as a non-transitory computer-readable recording medium having recorded thereon a program for causing a computer to execute steps included in the cognitive function evaluation method.

Thus, the cognitive function evaluation method according to the embodiment can be executed easily using a computer.

(Variations)

A cognitive function evaluation system according to each of Variations 1 and 2 of the embodiment will be described below. The same components as those in the embodiment are given the same reference marks, and repeated description may be omitted or simplified.

Figure 11:
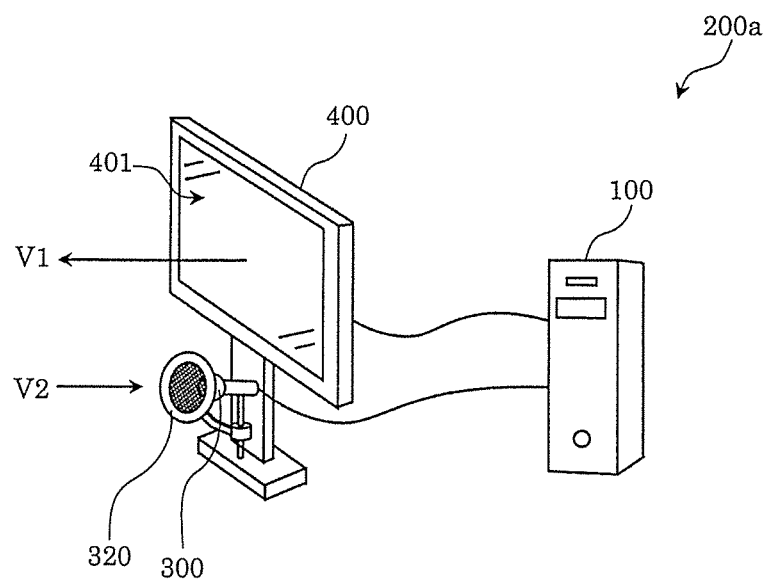
FIG. 11 is a diagram illustrating a structure of a cognitive function evaluation system according to Variation 1 of the embodiment.

FIG. 11 is a diagram illustrating a structure of a cognitive function evaluation system according to Variation 1 of the embodiment.

Cognitive function evaluation system 200*a* according to Variation 1 of the embodiment includes cognitive function evaluation device 100, sound collection device 300, and display device 400, as with cognitive function evaluation system 200 according to the embodiment. For example, cognitive function evaluation system 200*a* may include pop filter 320 so as to cover sound collection device 300.

In cognitive function evaluation system 200*a*, sound collection device 300 has directivity. Sound collection device 300 and display device 400 are arranged in a state in which the direction in which sound collection device 300 has maximum sensitivity (sound collection direction V2 in FIG. 11) and normal direction V1 of display surface 401 on which display device 400 displays task information match. Specifically, sound collection device 300 and display device 400 are placed on a stationary object such as a desk so that normal direction V1 and sound collection direction V2 are parallel to each other. Sound collection device 300 and display device 400 may be fixed to a building material or the like. Cognitive function evaluation system 200a may include a fixture for fixing the positional relationship between sound collection device 300 and display device 400.

Thus, even in the case where subject U utters speech while seeing display device 400, sound collection direction V2 and the direction in which subject U utters speech match easily. Such a positional relationship in cognitive function evaluation system 200a facilitates accurate detection of speech of subject U by sound collection device 300.

A cognitive function evaluation system according to Variation 2 of the embodiment will be described below.

Figure 12:
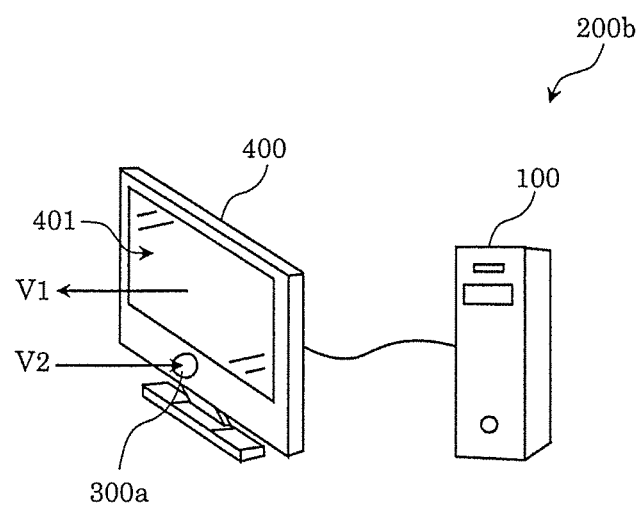
FIG. 12 is a diagram illustrating a structure of a cognitive function evaluation system according to Variation 2 of the embodiment.

FIG. 12 is a diagram illustrating a structure of a cognitive function evaluation system according to Variation 2 of the embodiment.

Cognitive function evaluation system 200b according to Variation 2 of the embodiment includes cognitive function evaluation device 100, sound collection device 300a, and display device 400, as with cognitive function evaluation system 200 according to the embodiment.

Sound collection device 300a is a microphone that detects speech uttered by subject U and outputs speech data indicating the detected speech to cognitive function evaluation device 100, as with sound collection device 300. Sound collection device 300a has directivity, as with sound collection device 300 in cognitive function evaluation system 200a according to Variation 1.

In cognitive function evaluation system 200b, sound collection device 300a and display device 400 are integrated as a single device. Specifically, sound collection device 300a and display device 400 are arranged in the same housing. By setting normal direction V1 and sound collection direction V2 to match each other in a production process of integrating sound collection device 300a and display device 400, a mismatch between normal direction V1 and sound collection direction V2 is prevented when subject U uses cognitive function evaluation system 200b.

Other Embodiments

Although the cognitive function evaluation system, etc. according to each of the embodiment and Variations 1 and 2 of the embodiment have been described above, the present invention is not limited to the foregoing embodiment.

In the foregoing embodiment, the cognitive function evaluation device evaluates subject U as NC, MCI, or AD, as a specific example of cognitive function evaluation. The cognitive function evaluation device is, however, not limited to evaluation of NC, MCI, or AD. For example, the cognitive function evaluation device may evaluate the degree of intoxication of subject U.

In the foregoing embodiment, Alzheimer's dementia is used as a specific example of a symptom of cognitive function decrease. The cognitive function is the ability to recognize, remember, and judge, and dementia shows a symptom of a decrease in the cognitive function. Accordingly, the degree of the cognitive function evaluated by the cognitive function evaluation device is not limited to Alzheimer's dementia, and may be, for example, vascular dementia.

In the foregoing embodiment, to evaluate the degree of the cognitive function of subject U, data indicating the relationship between the score of the MoCA test and the feature value of the formant is stored in storage unit 150 beforehand as reference data 151. The reference data is, however, not limited to data indicating the relationship between the MoCA test and the feature value of the formant, as long as it is data with which the degree of the cognitive function can be evaluated by checking with the feature value of the formant. For example, the reference data may be data indicating the relationship between the score of Mini-Mental State Examination (MMSE) and the feature value of the formant such as frequency.

The present invention may be implemented as a program for causing a computer to execute steps performed by the cognitive function evaluation device. The present invention may be implemented as a computer-readable recording medium such as CD-ROM on which the program is recorded. The present invention may be implemented as information, data, or a signal indicating the program. The program, the information, the data, and the signal may be distributed via a communication network such as the Internet.

In the case where text uttered by the subject is a foreign language, the frequency of a formant may be calculated from speech containing "a", "i", "u", "e", "o", or the like.

In the foregoing embodiment, the cognitive function of the subject is evaluated by calculating the feature value using only the speech data obtained from the subject. Alternatively, evaluation may be performed in combination with another known data with which the cognitive function can be evaluated. For example, it is known that the cognitive function and gait data relating to gait such as stride length, step width, and walking speed correlate with each other. By using the gait data of the subject in combination with the speech data of the subject evaluated in the foregoing embodiment for cognitive function evaluation, the cognitive function of the subject can be evaluated more accurately.

The foregoing embodiment describes a plurality of examples of a feature value calculated by the calculation unit. The evaluation unit may evaluate the cognitive function of the subject from a plurality of different feature values calculated by the calculation unit. The evaluation unit may weight each feature value, and evaluate the cognitive function of the subject. Any coefficients may be used in the weighting by the evaluation unit.

Other modifications obtained by applying various changes conceivable by a person skilled in the art to the embodiments and any combinations of the structural elements and functions in the embodiments without departing from the scope of the present invention are also included in the present invention.

The invention claimed is:

1. A cognitive function evaluation device, comprising:
a display device configured to display task information for a speech uttered by a subject, the task information including displayed text of one or more of a tongue twister, and random vowels particular to a memory of the subject;
an obtainment unit operably connected to a sound collection device including a microphone, the obtainment unit configured to obtain speech data indicating the speech uttered by the subject into the microphone;

wherein the sound collection device includes a sound barrier surrounding the microphone;
a processor configured to,
extract a plurality of vowels from the speech data obtained by the obtainment unit,
calculate, for each of the plurality of vowels, a feature value based on a frequency and an amplitude of at least one formant obtained from a spectrum of the vowel, and
evaluate a cognitive function of the subject from the feature value calculated; and
an output unit configured to output an evaluation result of the processor and an image of the evaluation result using the display device, the obtainment unit further configured to display to the subject a recommendation to seek medical attention alongside the image of the evaluation result, the recommendation based on the evaluation result;
wherein the processor is further configured to:
calculate frequencies and amplitudes of a plurality of second formants at predetermined time intervals in the spectrum, as the frequency and the amplitude of the at least one formant; and
calculate, as the feature value, an amount of change over time of the frequencies and the amplitudes of the plurality of second formants calculated.

2. The cognitive function evaluation device according to claim 1, wherein the processor is further configured to:
calculate, as the feature value, the amount of change over time of the frequencies, a standard deviation of the frequencies and the amplitudes of the plurality of second formants.

3. The cognitive function evaluation device according to claim 1, wherein the processor is further configured to:
calculate frequencies and amplitudes of a plurality of first formants, as the frequency and the amplitude of the at least one formant; and
calculate the frequencies of the second formants relative to the frequencies of the first formants and the amplitudes of the second formants relative to the amplitudes of the first formants, as the feature value.

4. The cognitive function evaluation device according to claim 1, further comprising:
a storage unit configured to store reference data indicating a relationship between information about a feature value of a person and a cognitive function of the person, wherein the processor is further configured to evaluate the cognitive function of the subject, by checking the feature value of the subject against the reference data stored in the storage unit.

5. The cognitive function evaluation device according to claim 1, wherein the output unit is configured to output task information for causing the subject to utter specific speech, and the processor is configured to further calculate, as the feature value, at least one of:
a time from when the output unit outputs the task information to when the obtainment unit obtains the speech data;
a temporal change of an amplitude indicated by the speech data;
and whether an answer to the task information is correct.

6. A cognitive function evaluation system, comprising:
the cognitive function evaluation device according to claim 1;
the microphone;
and a display device that displays the evaluation result output from the output unit.

7. The cognitive function evaluation system according to claim 6, wherein the microphone has directivity, and
the microphone and the display device are arranged in a state in which a direction in which the microphone has maximum sensitivity and a normal direction of a display surface of the display device match.

8. A cognitive function evaluation method, comprising:
displaying, with a display device, task information for a speech uttered by a subject, the task information including displayed text of one or more of a tongue twister, and random vowels particular to a memory of the subject;
obtaining speech data using a sound collection device including a microphone, the speech data indicating the speech uttered by the subject into the microphone, the sound collection device including a sound barrier surrounding the microphone;
extracting a plurality of vowels from the speech data obtained in the obtaining, and calculating, for each of the plurality of vowels, a feature value based on a frequency and an amplitude of at least one formant obtained from a spectrum of the vowel;
evaluating a cognitive function of the subject from the feature value calculated in the calculating,
outputting an evaluation result and an image of the evaluation result using the display device,
and outputting, using the display device, a recommendation to seek medical attention alongside the image of the evaluation result, the recommendation based on the evaluation result;
wherein the calculating includes:
calculating frequencies and amplitudes of a plurality of second formants at predetermined time intervals in the spectrum, as the frequency and the amplitude of the at least one formant; and
calculating, as the feature value, an amount of change over time of the frequencies and the amplitudes of the plurality of second formants calculated.

9. A non-transitory computer-readable recording medium having recorded thereon a program for causing a processor to execute the cognitive function evaluation method according to claim 8.

10. A cognitive function evaluation device, comprising:
a display device configured to display task information for a speech uttered by a subject, the task information including displayed text of one or more of a tongue twister, and random vowels particular to a memory of the subject;
an obtainment unit operably connected to a sound collection device including a microphone, the obtainment unit configured to obtain speech data indicating the speech uttered by the subject;
wherein the sound collection device includes a sound barrier surrounding the microphone;
a processor configured to,
extract a plurality of vowels from the speech data obtained by the obtainment unit,
calculate, for each of the plurality of vowels, a feature value based on a frequency and an amplitude of at least one formant obtained from a spectrum of the vowel, and
evaluate a cognitive function of the subject from the feature value calculated; and
an output unit configured to output an evaluation result of the processor and an image of the evaluation result using the display device, the obtainment unit further configured to display to the subject a recommendation to seek medical attention alongside the image of the evaluation result, the recommendation based on the evaluation result;

wherein the processor is configured to:
- calculate a frequency and an amplitude of a first formant and a frequency and an amplitude of a second formant from the spectrum, as the frequency and the amplitude of the at least one formant; and
- calculate the frequency of the second formant relative to the frequency of the first formant and the amplitude of the second formant relative to the amplitude of the first formant, as the feature value.

\* \* \* \* \*